United States Patent [19]

Pribat et al.

[11] Patent Number: 5,087,275
[45] Date of Patent: Feb. 11, 1992

[54] ELECTROCHEMICAL SENSOR HAVING MICROCAVITIES

[75] Inventors: Didier Pribat, Paris; Joël Perret, Plaisir; Jean-Claude Rouffy, Poissy; Gonzalo Velasco, Paris, all of France

[73] Assignee: Thomson-CSF, Paris, France

[21] Appl. No.: 544,887

[22] Filed: Jun. 28, 1990

Related U.S. Application Data

[62] Division of Ser. No. 245,731, Sep. 19, 1988, Pat. No. 4,956,073.

[30] Foreign Application Priority Data

Sep. 22, 1987 [FR] France ............... 8713058

[51] Int. Cl.⁵ ............................................. B01D 15/08
[52] U.S. Cl. ............................................. 55/386; 55/67
[58] Field of Search ........................ 55/67, 197, 386

[56] References Cited

U.S. PATENT DOCUMENTS

| | | | |
|---|---|---|---|
| 3,417,548 | 12/1968 | Thompson | 55/67 |
| 3,449,938 | 6/1969 | Giddings | 55/67 X |
| 3,748,833 | 7/1973 | Karas et al. | 55/197 |
| 3,949,806 | 4/1976 | Dunges | 55/197 X |
| 4,271,000 | 6/1981 | Croset et al. | 204/426 |
| 4,272,350 | 6/1981 | Croset et al. | 204/426 |
| 4,488,920 | 12/1984 | Danis | 264/59 X |
| 4,575,424 | 3/1986 | Allington et al. | 55/67 X |
| 4,668,374 | 5/1987 | Bhagat et al. | 204/412 |
| 4,741,817 | 5/1988 | Croset et al. | 204/426 X |
| 4,935,040 | 6/1990 | Goedert | 55/197 |

FOREIGN PATENT DOCUMENTS

| | | | |
|---|---|---|---|
| 636078 | 2/1962 | Canada | 55/386 |
| 47687 | 3/1982 | European Pat. Off. . | |
| 52542 | 5/1982 | European Pat. Off. . | |
| 104636 | 4/1984 | European Pat. Off. . | |
| 140295 | 5/1985 | European Pat. Off. . | |
| 144057 | 6/1985 | European Pat. Off. . | |
| 203351 | 12/1986 | European Pat. Off. . | |
| 218357 | 4/1987 | European Pat. Off. . | |
| 1113319 | 8/1961 | Fed. Rep. of Germany | 55/386 |
| 60-142254 | 7/1985 | Japan | 55/386 |
| 60-229340 | 10/1985 | Japan | 55/386 |
| 60-229342 | 10/1985 | Japan | 55/386 |
| 61-142462 | 6/1986 | Japan | 55/386 |
| 61-233365 | 10/1986 | Japan | 55/386 |
| 61-233366 | 10/1986 | Japan | 55/386 |
| 62-103569 | 5/1987 | Japan | 55/386 |
| 399780 | 3/1966 | Switzerland | 55/197 |

*Primary Examiner*—Robert Spitzer
*Attorney, Agent, or Firm*—Oblon, Spivak, McClelland, Maier & Neustadt

[57] ABSTRACT

A method for making a microcavity in an enamel layer is disclosed. For this purpose, a layer of a carbon-based material with the dimensions of the microcavity to be obtained is provided. This layer is coated with an enamel except in a limited zone. The unit is heated to high temperature so as to cause combustion of the carbon-based material. The combustion gases escape through the reduced zone.

2 Claims, 9 Drawing Sheets

ELECTROCHEMICAL SENSOR HAVING MICROCAVITIES

This is a division of application Ser. No. 245,731, filed Sept. 19, 1988, now U.S. Pat. No. 4,956,073.

BACKGROUND OF THE INVENTION

1. Field of the Invention

The invention concerns a method for making microcavities on a substrate. It can be applied to an electrochemical sensor for measuring the concentration of reactive species with reduced response time and, more particularly, to a sensor made with thin film or thick film type technology on a substrate that is electrically insulating and chemically inert at high temperature. It also concerns a method for making a sensor of this type.

The invention can also be applied, inter alia, to the making of a gas-phase chromatograph and, especially, to the separation column of a chromatograph of this type.

2. Description of the Prior Art

One of the well-known groups of electrochemical sensors works on the principle of the concentration cell and measures the partial pressure of one or more species of the gaseous mixture to be analyzed. This gaseous mixture, which is present in a first compartment and is, for example, an oxygen/inert gas mixture, is separated from a reference medium by the wall of a solid electrolyte, each face of which has an electrode. As is well known, the equations that govern the working of these sensors are: at the electrodes/electrolyte interfaces:

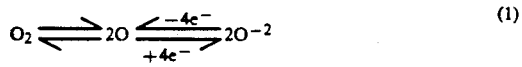

$$O_2 \rightleftharpoons 2O \underset{+4e^-}{\overset{-4e^-}{\rightleftharpoons}} 2O^{-2} \quad (1)$$

the voltage $V_{E1/E2}$ which then develops; between the electrodes is given by Nernst's law:

$$V_{E1/E2} = \frac{RT}{4F} \operatorname{Ln} \frac{P_1}{P_2} \quad (2)$$

with

R = perfect gas constant = 8.314 J.(mole. K)$^{-1}$
F = Faraday No. = 96490 Coulombs
T = absolute temperature in degrees Kelvin
$P_1$ and $P_2$ = partial pressures of media 1 and 2 in the compartments 1 and 2.

Thus, knowledge of the temperature and of one of the partial pressures enables the unambiguous determining of the other partial pressure.

Should the mixture be reactive, for example, if it is a mixture of $O_2$ and CO, and if the electrode is a catalyst of the reaction of these gases, the following reaction occurs:

$$2CO + O_2 \rightleftharpoons 2CO_2 \quad (3)$$

and, finally, if the combustion is total, until reversible thermodynamic equilibrium is achieved, the following relationship is verified:

$$\frac{[P\,CO]\,[PO_2]^{\frac{1}{2}}}{[PCO_2]} = K(T) \quad (4)$$

with K(T) being a coefficient of equilibrium depending on the temperature, and P CO, P $O_2$, P $CO_2$, being the partial pressures of carbon dioxide, oxygen and carbonic gas.

In applications concerning the regulation of automobile engines with spark ignition, to determine the partial pressure of oxygen at the exhaust (medium 1 for example), knowing the reference pressure (medium 2 which is generally air) in removing the need to measure or regulate the temperature, use is made of the fact that, if the exhaust gases are brought to thermodynamic equilibrium (end of combustion), the value of the partial pressure of oxygen, as shown in FIG. 1, varies by some fifteen orders of magnitude when the mixture feeding the cylinders passes through the stoichiometric state.

Thus, in the above-described Nernst formula, a voltage leap is observed when the mixture passes the stoichiometric state $\Delta V = RT/4F$ log $PO_2$rich/$PO_2$poor); if the temperature is in the range of 800° C., the term RT/4F is of the order of 50 mV and the $\Delta V$ will be greater than 750 mV.

Sensors of this type, called stoichiometrical sensors, generally consist of a glove finger made of stabilized zircon. The external wall, provided with a porous platinum electrode (measuring electrode), is in contact with the gas for which it is sought to analyze the oxygen content and the inner wall, also provided with a platinum electrode (reference electrode), is in contact with a reference gas, generally air. The platinum of the measuring electrode catalyzes the end of combustion of the exhaust gases for example and, in order not to saturate the platinum, it is encapsulated by means of a porous diffusion layer which has the main effect of limiting the flow of gases reaching the catalytic sites of the platinum electrode.

FIG. 2 shows a few typical responses of these glove finger sensors using air as a reference.

However, the making of sensors of this type may take different forms. FIGS. 3 and 4 show examples of methods for making these sensors obtained by successive deposits (thin layers or thick layers) of ceramic and metallic materials on an electrically insulating substrate. According to FIG. 3, there is a known method to make an electrochemical sensor comprising a solid electrolyte EL on a substrate Sb. This electrolyte may be made of zircon, thoria or cerium oxide stabilized by one or more elements belonging to columns II$_A$ and III$_B$ of the periodic classification of elements. It may be made as a thin layer or a thick layer, or it may be massive.

Electrodes E2/P2 and E1/P1 are deposited on the electrolyte EL and on the substrate Sb. The electrodes E1/P1 and E2/P2 are located in one and the same plane. The electrode E1/P1 combines the functions of an electrode and a reference medium. The electrode E1/P1 is further protected from the external environment by an impervious and inert insulating material S1 which coats it. It is possible, for example, to use an association of the type Ni/NiO or Pd/PdO to make this electrode/reference medium. The electrode E2/P2 has two zones and communicates directly with the medium to be analyzed in which there flows the gaseous mixture G through a hole made in the insulating body S1 which also covers it. In the first zone Ct, the electrode is not in contact with the electrolyte EL. The fluid to be analyzed must flow through the zone Ct which takes the place of a catalyst. In this zone, the reactive species of the mixture to be analyzed (for example, in the case of exhaust gases: CO and $O_2$) are brought to full thermodynamic equilibrium before they have reached the electrochemical cell itself:

E2/P2−EL−E1/P1

P2 represents the partial pressure of oxygen after catalysis in the real medium to be analyzed. The catalysis which enables obtaining thermodynamic equilibrium is achieved by the fact that the fluid flows through the catalyst in a direction parallel to the plane of the electrodes. The electrodes are extended outwards by metallic links to which the contacts C1 and C2 may be soldered. These links are made with platinum veneer for example. In one practical embodiment, the metallic links and the electrodes are made so as to form a single part. The substrate Sb may consist of a material (such as corundum) which insulates well at the operating temperature of the device and gives the unit mechanical strength. The face of the substrate 1 opposite the electrochemical cell has a heating resistor RC which enables accelerating the reaction.

The deposits can be made by well known techniques, such as: vacuum deposition (cathode spraying, evaporation), vapor phase deposition, electrochemical deposition or ion implantation or by a combination of two or more of these techniques. For a metal/oxidated metal reference mixture, such as Pd/PdO, the response, in voltage, to a temperature of about 800° C. is shown in FIG. 2 for the corresponding temperature.

The descriptions of sensors thus made will be found in the French patent Nos. 2441 164 and 2 444 272.

FIG. 5 shows another embodiment of a sensor according to the prior art.

This figure repeats the elements illustrated with reference to FIG. 3: the measuring cell E1/P1−El1−E2/P2, deposited in thin or thick layers or massively on a substrate Sb, the catalysis region Ct and the test samples intake region $P_{es}$ where the interactions with the gaseous mixture to be analyzed take place. In fact, in the example described, these latter two regions consist of an extension of the measuring electrode E2/P2. The output signal VS of the sensor is transmitted to external circuits (not shown) by connections C1 and C2. The two electrodes E1/P1 and E2/P2 should at least be shielded by an impervious and inert insulating jacket S1, made of enamel for example.

According to the sensor of FIG. 5, an additional electrochemical cell is integrated into the sensor and comprises a solid electrolyte El2 inserted between two electrodes E3 and E4. In the embodiment of FIG. 5, and according to the first approach, the second electrode E4 is identified with the extension of the measuring electrode E2. The cell is flush with the surface of the insulating material S1 so as to communicate with a medium containing oxygen. This medium may be the medium Mex in which there flows the gaseous mixture G to be analyzed. The cell E3−El2−E4 is supplied with a control current Ip by means of connections C3 and C4, C4 being identified with C2. The face of the substrate opposite to the electrochemical cell also has a heating resistor RC.

Referring again to the above description, it is immediately seen that the cell E3−El2−E4, working as an ion pump, modifies the oxygen composition of the test sample let the sensor, namely the oxygen composition of the gaseous mixture flowing towards and through the catalysis zone Ct to subsequently reach the measuring cell E2/P2−El1−E1/P1, and does this modification as a function of the amplitude and bias of the current Ip. It follows that this cell produces an output signal VS which flips over, no longer when the stoichiometric state of the mixture G is reached but "before" or "after" said stochiometric state, the lag on either side of the stoichiometric state being defined continuously by the amplitude and bias of the control current Ip. FIG. 6 shows a few typical responses of this type of sensor as a function of the bias current Ip.

A description of a sensor of this type will be found in French patent Nos. 2 494 445 and 2 442 444.

In prior art sensors such as those described above, the gaseous mixture is thus catalyzed, making it possible to obtain a thermodynamic equilibrium, and to do so before measuring the concentration of the species constituting the mixture. This catalysis is performed in the course of a diffusive path in a porous body. This path is laid down by the geometry of the sensor and the different deposits constituting the sensor.

This diffusive path causes a delay in the analysis of the gas. This delay is due to the time taken by the different molecules to move forward between the place where they are incorporated in the porous material (test sample window G) and the place where they will fix the electrochemical potential of the working electrode. This delay in the analysis of the gases can penalize the total response time of the sensor (since this sensor furthermore brings into play phenomena in which the different electrodes are placed in equilibrium). This diffusion time, with a delay $\tau$, can be evaluated by the formula: $\tau = l^2/D$ where $l$ is the length of the diffusive path and D is the coefficient of diffusion of the gaseous species in the porous medium.

If the mean diameter of the pores of the diffusive medium is in the range of the length of the mean free path of the gas molecules at working temperature and pressure (between $10^2$ and $10^3$ angstroms in an automobile exhaust silencer for example), the diffusion takes places according to a principle called Knudsen's flow according to which the interaction of the molecules takes place preponderantly with the walls of the pores. In this case, the expression of the diffusion coefficient is:

$$Dk = \tfrac{2}{3} a(8kT/\pi M)^{\tfrac{1}{2}}$$

where $a$ is the mean radius of the pores, $k$ is Boltzmann constant, T is the absolute temperature and M is the molecular mass of the diffusing gaseous species. For example, the coefficient of diffusion of oxygen at 1000° K. and at atmospheric pressure in a porous medium where the mean diameter of the pores is $10^3$ angstroms is about $10^{-2}$ cm$^2$sec$^{-1}$. The diffusion time associated with a diffusion length of about 100 um is about 100 ms in these conditions.

It might be further observed that, in Knudsen's formula, only purely mechanical interactions between the gas and the walls of the pores are taken into account.

Now, when reactive gases such as CO and $O_2$ are made to diffuse in a porous medium consisting of oxides or metal/oxide (Cermet) mixtures, the impacts of the gas molecules on the walls of the pores are accompanied by a retention time, corresponding to a transient adsorption of the gas molecules at the faults on the surface which are always present in oxide or metal polycrystals. Thus, the molecules move forward by successive adsorption and desorption processes: the diffusion time of the gas molecules in question is thereby considerably increased and may go up to several seconds for a diffusion length always equal to 100 μm.

If, on the other hand, the diffusive medium is such that the mean size of the pores is far greater than the mean free path of the gas molecules in the medium at the pressure and temperature considered, the molecules will interact with one another preponderantly, and the effect of the walls of the pores will tend to disappear. In this case, the diffusion occurs by successive impacts of the diffusing gas molecules on the molecules of the carrier gas. The diffusion coefficient of the gas i in a monomolecular carrier gas j is then written in a simplified way as follows $$Dij = K \frac{[T^3 (Mi + Mj)/2MiMj]^{\frac{1}{2}}}{p\delta ij}$$

where the Mi,j are molecular masses of the gases i and j, T is the absolute temperature, p is the total pressure, 6ij is the diameter of collision and K is a constant. For example, the diffusion coefficient of oxygen at 1000° K. in nitrogen is about $1.6 \text{ cm}^2.\text{sec}^{-1}$. Thus, the diffusion time associated with a diffusive length of about 100 μm is, in these conditions, about 100 μsec, i.e. at least 100 times smaller than in the preceding case considered.

It would therefore seem, in the light of these assessments, that the more the diffusive mode in the porous limiting layer is of a molecular type (the second example described above), the shorter will be the associated diffusion time in the present example, and the shorter will be the response time of the sensor.

The invention therefore concerns a sensor in which the molecular diffusion mode is favored in order to reduce the diffusion time of the gas molecules and, correlatively, in order to reduce the total response time of the sensor.

SUMMARY OF THE INVENTION

The invention concerns a method for making microcavities on a first layer of material covered with at least one second layer of material, said method comprising the following steps:

the making, on the first layer of material, of at least one element having the shapes and dimensions of the microcavity or microcavities to be made, the material forming said element being volatile or combustible through heating;

the making of the second layer on the entire said element and of the first layer in such a way that at least one zone of the element is not coated with the second layer;

the heating of the unit thus obtained to a temperature enabling the evaporation or combustion of the material of the element, the evaporation or combustion products leaving the microcavity to be obtained through that zone of the element which is not covered by the second layer.

The invention also relates to an electrochemical sensor for the measurement of relative concentrations of species contained in a fluid mixture comprising:

at least one solid electrolyte which is an ion conductor of one of the species of the fluid mixture or of an ion capable of reacting with this species;

a first partial pressure internal reference electrode in contact, by one of its faces, entirely or partly, with the solid electrolyte;

a second measuring electrode in contact, by one of its faces, entirely or partially, with the solid electrolyte and receiving the fluid mixture to be analyzed;

a layer of an encapsulating material made of an inert material which is impervious to the species present in the fluid mixture, coating the first electrode, the second electrode and the solid electrolyte, and having one access hole enabling the fluid mixture to reach the second electrode;

said sensor also comprising a cavity partially covering the second electrode in that zone which covers the electrolyte, said cavity communicating through the access hole with the fluid mixture to be analyzed and having dimensions enabling a diffusion of a molecular type of fluid.

The invention also concerns a chromatograph made according to the method, comprising a substrate, a layer of impervious material, and a microchannel for the propagation of the gas, said microchannel being located between the substrate and said layer.

BRIEF DESCRIPTION OF THE DRAWINGS

The various objects and features of the invention will emerge more clearly from the following description, given by way of example and made with reference to the appended drawings, of which.

DETAILED DESCRIPTION OF THE INVENTION

Figure 1:
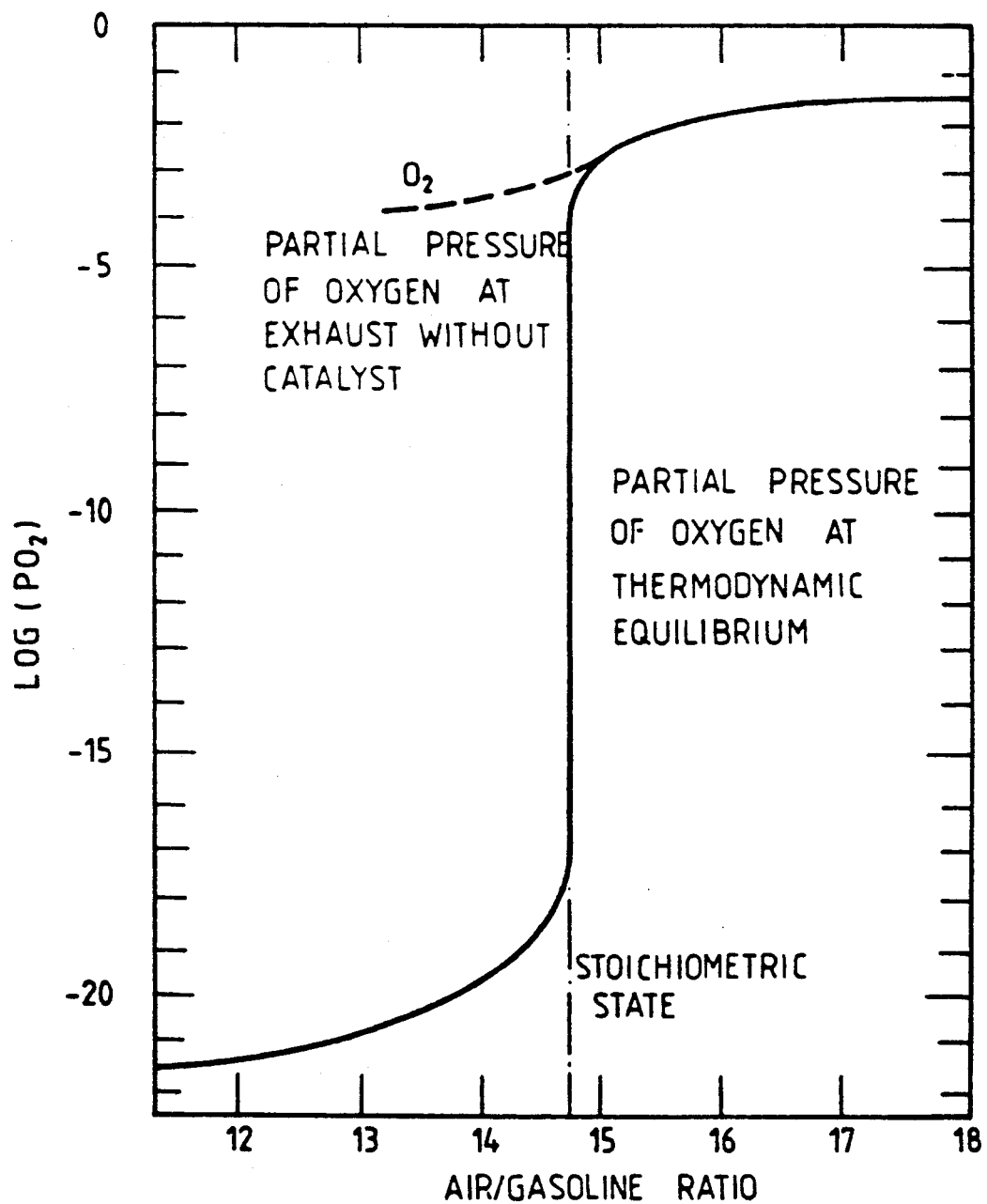
FIG. 1 is a graph of partial oxygen pressures in automobile exhaust gases.
Figure 2:
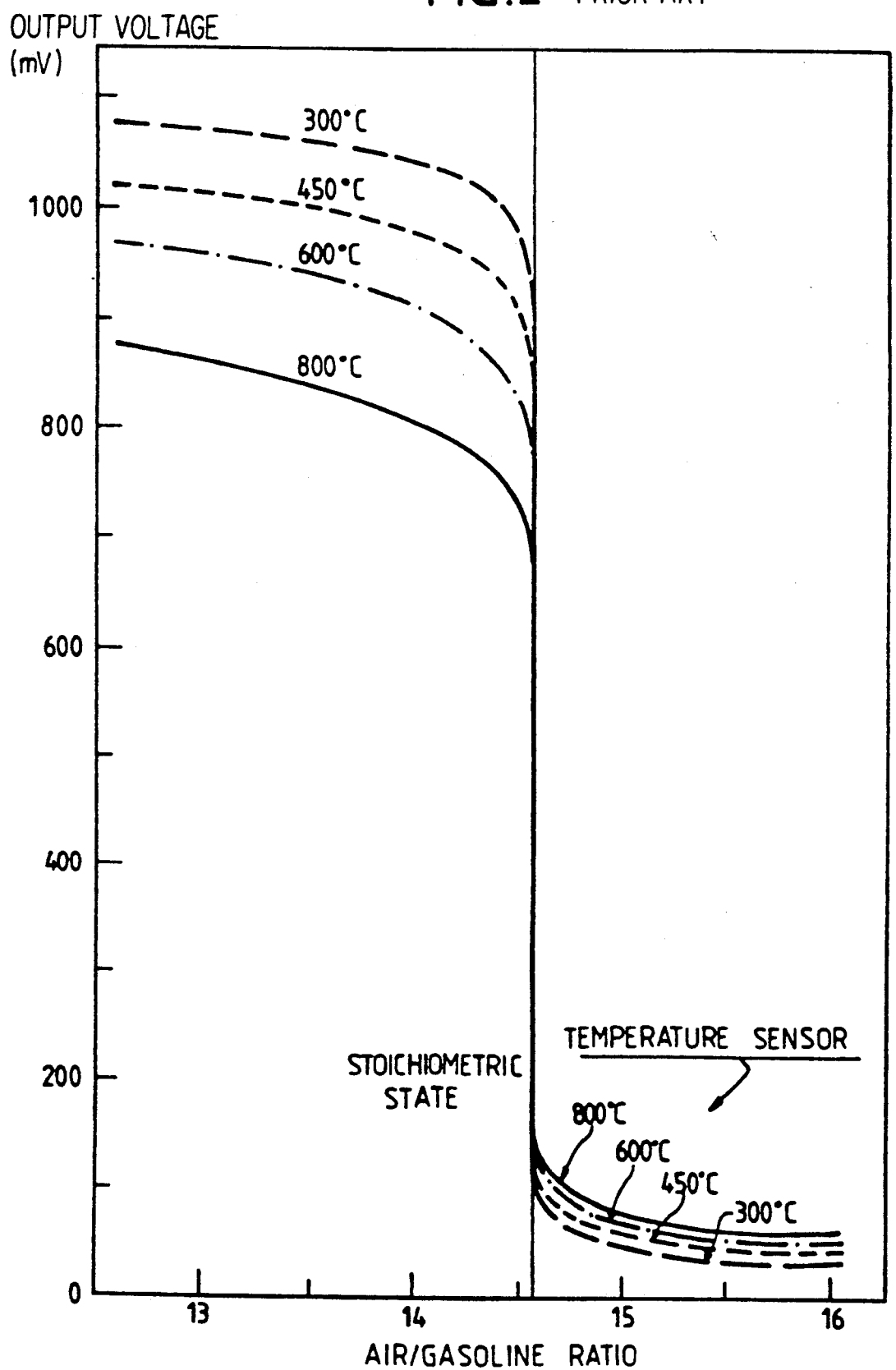
FIG. 2 shows voltage response curves for automobile sensors working with an air reference or a metal/oxydated metal mixture reference.
Figure 3:
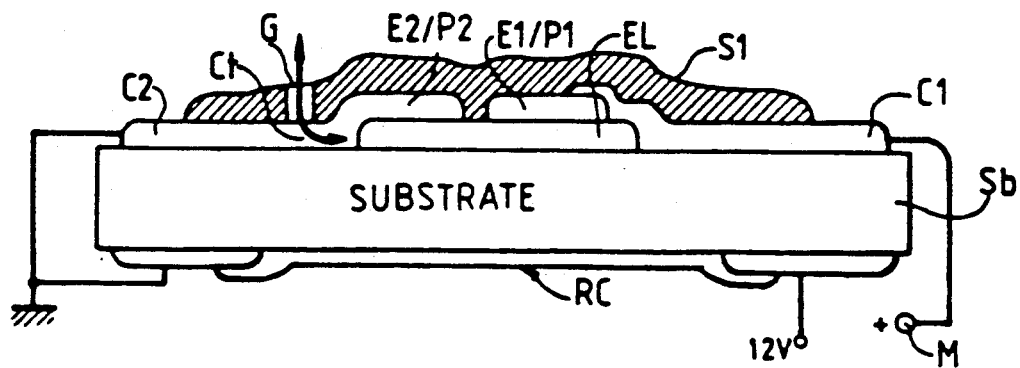
FIGS. 3 to 5 are embodiments of prior art sensors already described above.
Figure 4:
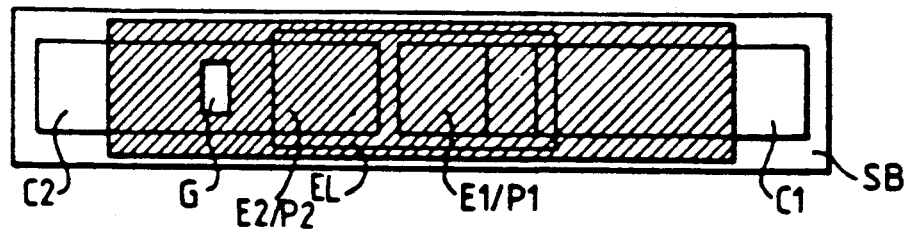
Figure 5:
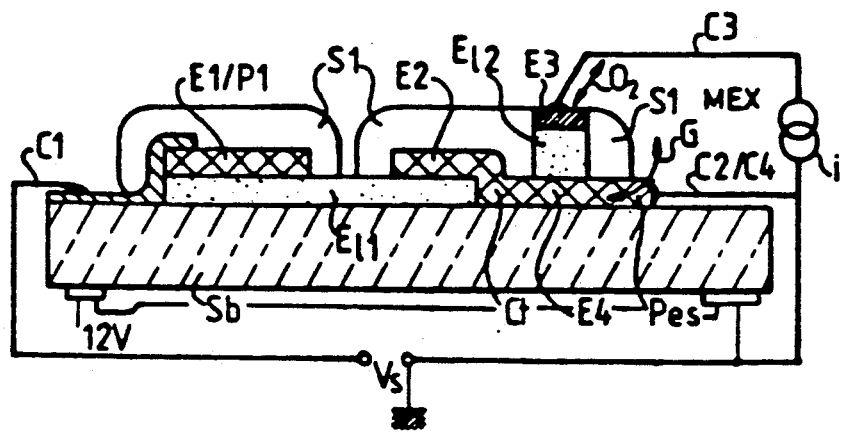
Figure 6:
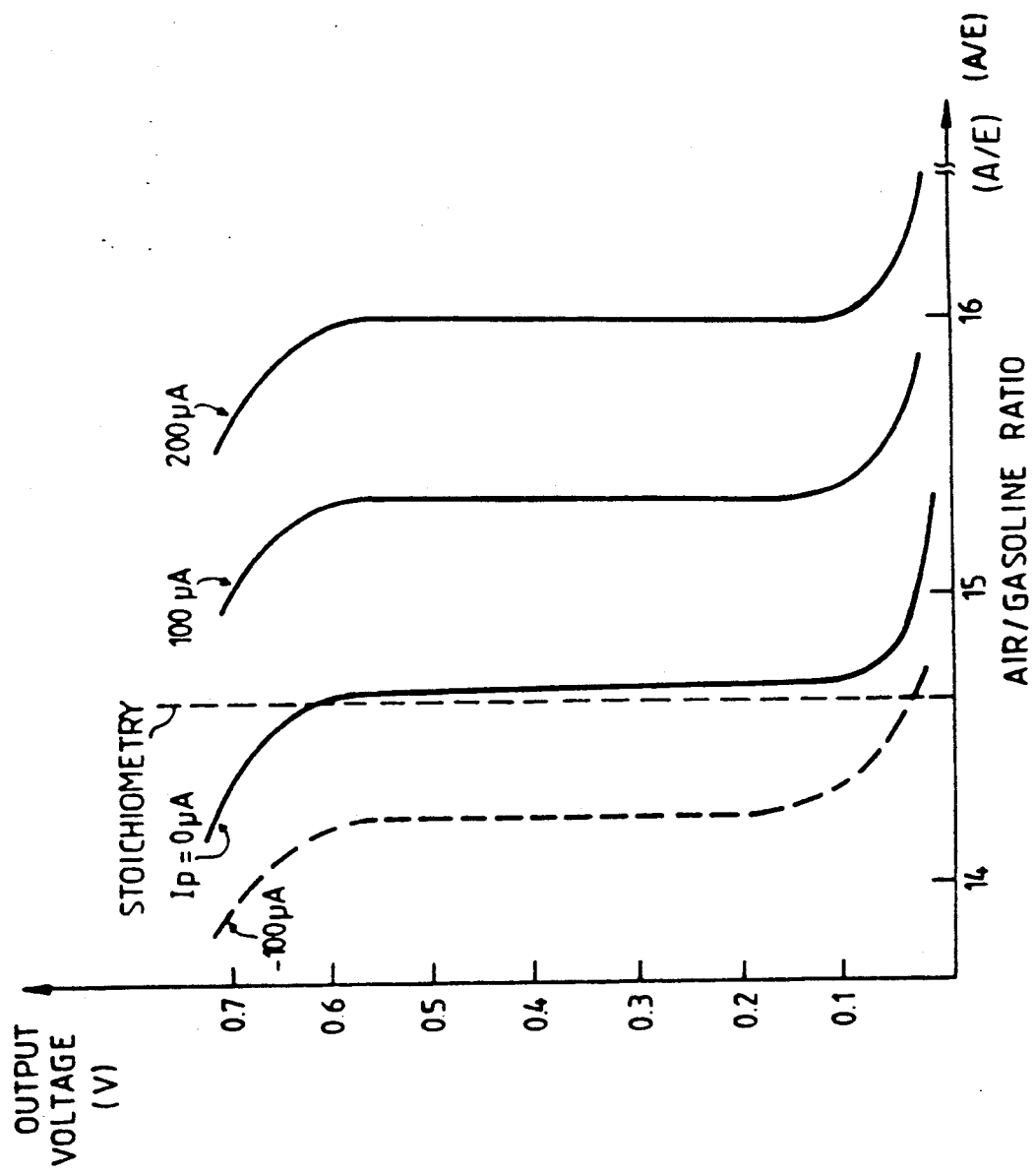
FIG. 6 shows response curves of a sensor according to FIG. 5.
Figure 7:
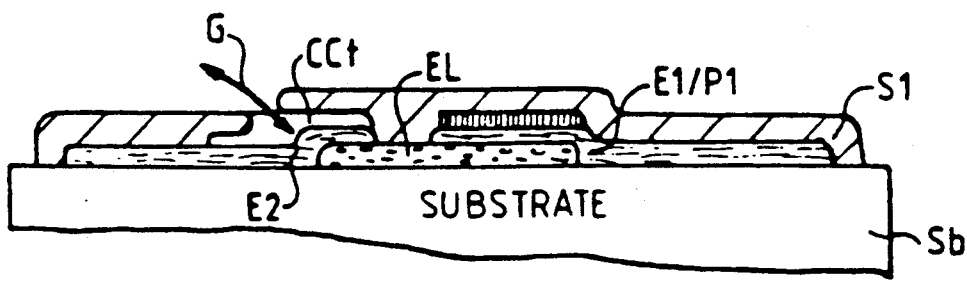
FIGS. 7 and 8 show an embodiment of a sensor according to the invention.
Figure 8:
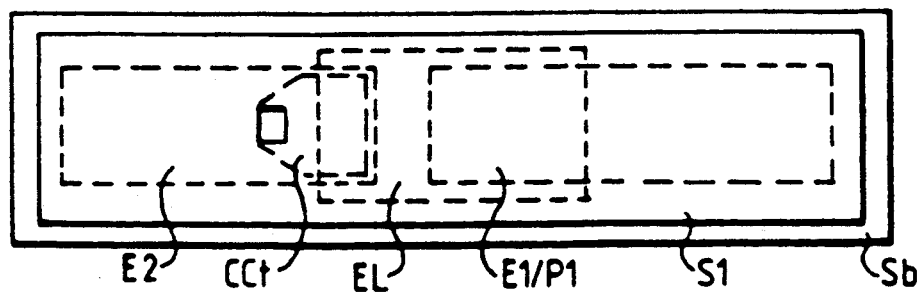

As prior art sensors, such as those shown in FIGS. 3 to 5, have already been described previously, we shall describe an embodiment of a sensor according to the invention such as the one shown in FIGS. 7 and 8.

As mentioned earlier, in a Knudsen mode of diffusion, the interaction of the molecules with the walls of the pores takes place not only by impacts but also by successive adsorption and desorption processes. The effect of this phenomenon will be to further reduce the value of the diffusion coefficient (and hence to increase the diffusion time) of reactive gases such as CO and $O_2$ in porous media based on refractory ceramics ($Al_2O_3$, $MgAl_2O_4$, etc.) and platinum forming excellent adsorption media.

In order to reduce the diffusion time, we shall therefore try to favor a molecular diffusion mode as compared with a Knudsen mode. However, it is difficult to obtain any significant increase in the porosity of the material in which the diffusion takes place because, when this is done, the effect of limitation of the gas flux is reduced by the porous layer and the adsorption sites of the working electrode are saturated, the effect of which is to notably reduce the catalytic activity of this same working electrode. It follows therefrom that the height of the signal delivered by the sensor is reduced, and that the voltage transition at the stoichiometric state is less steep: these are two effects that are sought to be avoided.

In order to preserve the effect of limitation of the flux and, at the same time, operate in a markedly molecular diffusion mode, the invention provides for replacing the porous body by a calibrated cavity of small thickness, with a width corresponding to the width of the working electrode and a length typically ranging between 50 and 750 μm.

FIGS. 7 and 8 represent an embodiment of the sensor according to the invention.

The general constitution of this sensor is similar to that of the sensor of FIG. 3. FIG. 7 shows the same elements with the same references as those of FIG. 3. This figure thus again shows the substrate Sb and the electrolyte EL, the reference electrode E1/P1, the working electrode E2/P2 and the encapsulating layer S1.

The sensor of FIG. 7 differs from the sensor of FIG. 3 in that a cavity CCt partially covers the electrode E2, especially in that part of the electrode which covers the electrolyte. This cavity communicates, through the access G, with the medium containing the gaseous mixture to be measured. The dimensions of this cavity are such that there is a molecular diffusion of the gaseous mixture inside this very same cavity. For example, the thickness is one to five micrometers and the width is the same as that of the measuring electrode.

In this way, the thermodynamic equilibrium of the gaseous mixture will be achieved swiftly in the cavity because, owing to its small thickness, the flow of molecules penetrating within is limited and the gaseous mixture will have to flow through the electrode E2 only along the thickness of the electrode (in the vertical in the figure) instead of having a diffusion parallel to the substrate as in the example of FIG. 3. The catalysis will take place during this diffusion along the thickness.

Figure 9:
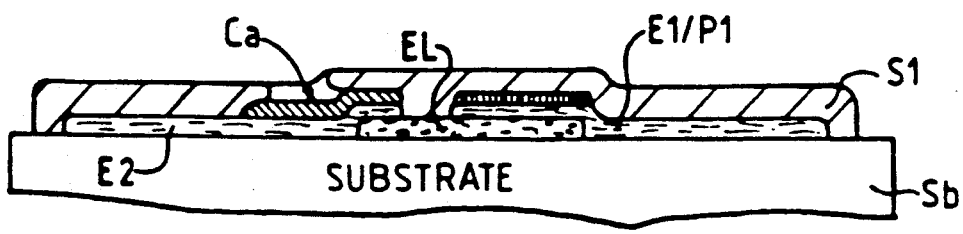
FIG. 9 shows a step in the obtaining of the method according to the invention.

Referring to FIG. 9, we shall describe a method for obtaining a sensor of this type and, especially, the method used to make the cavity CCt. For, the making of a cavity of this type lined with enamel S1 and with as small a thickness (1 to 5 micrometers) raises technological manufacturing problems. The invention makes it possible to resolve these problems.

According to the method of the invention, a layer of carbon Ca or any other organic material (photosensitive resist product, PMMA, polymers, etc.), with a thickness of 1 to 5 micrometers is deposited on the working electrode before the encapsulating enamel (see FIG. 9). This layer Ca is etched so as to give it the shape and thickness of the cavity to be obtained. Then, an encapsulating enamel of the devitrifiable glass type, known to those skilled in the art, is deposited. Once the encapsulating enamel has been deposited, the entire unit is baked in an oxygenated atmosphere (for example, air) so as to eliminate the carbon layer or organic material layer by combustion. Thus, under the enamel layer, a calibrated cavity is defined wherein the gas diffusion will have a markedly molecular tendency.

Should the different layers be deposited by silk screen process, a product is used for the layer Ca in a medium such as ethylcellulose+terpineol, with a carbon mass percentage varying between 10% and 75%.

As a non-restrictive example, a composition containing 30% of carbon by weight, 2.1% of ethylcellulose, 11.2% of a solvent such as dibutylphtalate and 56.7% of a solvent such as terpineol gives good results.

Thus, it is possible to make a cavity with a uniform thickness of 1 to 5 um throughout the surface of the working electrode.

The material used as the encapsulating enamel will preferably be a devitrifiable material so that it can withstand working temperatures equal to or greater than its baking and layering temperature (for example 900° C.) without changing shape or running for all that. This enables the cavity to preserve its thickness during operation and, therefore, enables the sensor to preserve its characteristics.

Finally, it may be noted that the use of carbon is preferred to that of any other organic material, because the latter can only burn and be converted into $CO_2$ unlike polymers and other organic derivatives which often start by cracking when they are heated.

The use of a sensor according to the invention enables a reduction in the response time of the sensors. Thus, a response time of 40 ms was obtained with a sensor according to the invention, while a response time of 100 ms and more was obtained when the diffusive channel was made of ceramic or cermet (ceramic/metal) with calibrated porosity. Although the invention has been described with reference to an example of a galvanic sensor, it can clearly be extended to all types of sensors and, especially, to resistive sensors.

In addition to its application to oxygen sensors of the galvanic or resistive type, such as the ones described above, the present invention also enables the manufacture of micro-channels which can be used, for example, in designing gas-phase microchromatographs, and especially separation columns for microchromatographs of this type.

A gas-phase chromatograph consists of a separating column, wherein the gaseous mixture to be analyzed is separated by diffusion in a carrier gas (generally helium). Each constituent element of the mixture thus separated then flows to a detection cell comprising, for example, an electrical resistor with a high temperature coefficient mounted in a Wheatstone bridge which identifies the constituent element in question by measurement of thermal conductivity.

The present invention concerns solely the "separating column" part of the chromatograph(or microchromatograph). As indicated above, the gaseous mixture is separated by diffusion in said column. If we refer to the expressions of the diffusion coefficients given above, either for diffusion governed by the Knudsen flow principle (Dk) or for molecular type diffusion (Dij), it is seen that the molecular mass i of the gas i to be examined, determines, at known and constant temperature and pressure values, the value of the diffusion coefficient of the species i, either in a porous medium or in a carrier gas j. When the diffusion mode is mixed, i.e. when there is neither a purely Knudsen type of diffusion nor a purely molecular type of diffusion, the diffusion coefficient of the gaseous species i,Di is expressed in the form $1/Di = 1/Dk + 1/Dij$.

In other words, in all possible cases of diffusion, the diffusion coefficient of a species i differs according to the molecular mass of this very same species.

If there is a separation column of appropriate length, and if a gaseous mixture is let in at the inlet of the column, these different gases will reach a detection cell located at the output of the column at times $t_i = l^2/D_i$ which are absolutely different and, consequently, the gases being separated can be analyzed and identified individually by measuring their thermal conductivity for example.

Figure 10:
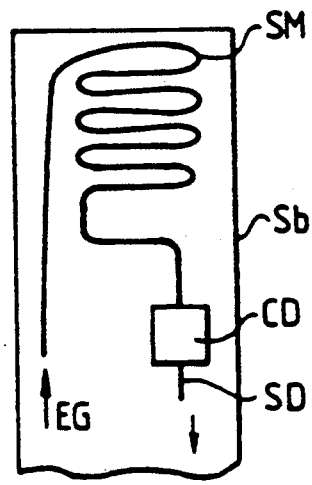
FIGS. 10 and 11 are simplified drawings of a chromatograph.
Figure 11:
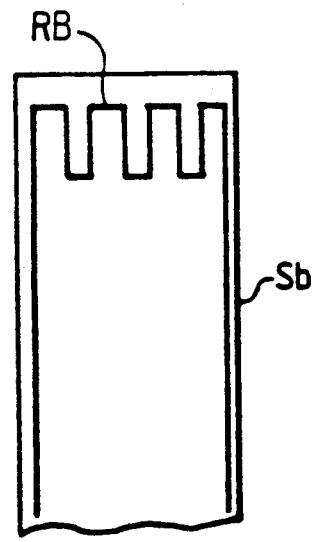

FIGS. 10 and 11 give simplified views of a microchromatograph of this type. FIG. 10 shows that a substrate Sb bears a serpentine tube or separating column SM on one of its faces. This tube or column has a gas inlet EG which is connected to a detector CD. After flowing into the detector, the gases are removed by the outlet SD. The gaseous mixture enters through the inlet EG and travels through the separating column SM. Each constituent element reaches the detector CD separately where it is identified and then evaluated by the outlet SD. Although this is not shown in FIG. 10, the separating column SM is coated with a devitrifiable enamel layer.

In FIG. 11, it can be seen that the other face of the substrate Sb carries a heating resistor RB, facing the separating column. This heating resistor RB enables acceleration of the diffusion and hence, a reduction in the reponse time of the microchromatograph.

Referring to FIGS. 12 to 21, we shall now describe an exemplary method for making the chromatograph separating column SM.

Figure 12:
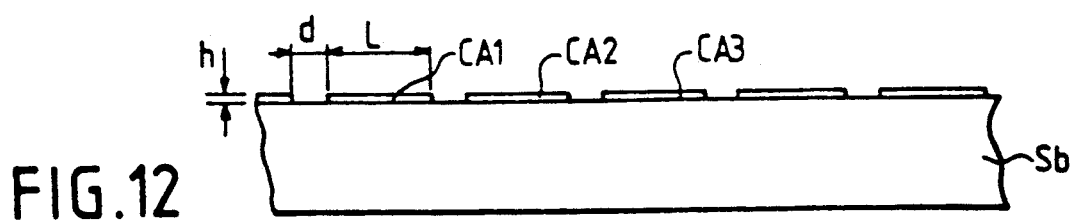
FIGS. 12 to 22 are steps in a method for making a chromatograph according to the invention.
Figure 13:
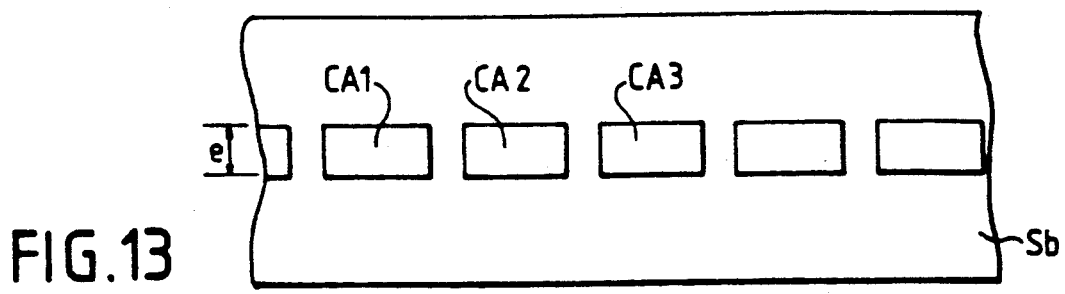
Figure 14:
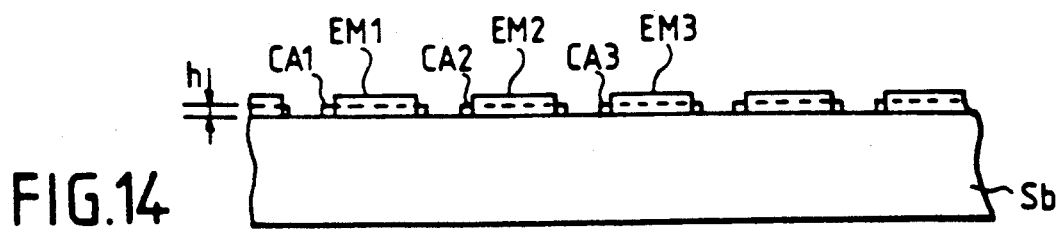

As shown in FIGS. 12 and 13, on a substrate Sb, pads CA1, CA2, CA3 are made. These pads are of a combustible or volatile material, for example a carbon-based material. These pads are aligned with the layout of the future separating column to be obtained.

As a non-restrictive example, their dimensions are:
length L=50 to 100 micrometers,
width W=10 to 20 micrometers or more,
thickness t=1 to 5 micrometers.
These pads are preferably all identical.

They are spaced out at a distance d which may be 2 to 5 micrometers for example, hence a distance that is very small when compared with the length L of each pad.

On each pad, there is made a layer of devitrifiable enamel, such as EM1 for CA1 and EM2 for CA2. Each layer leaves two ends free along the layout line of the separating column. Thus we get the configuration of FIG. 14.

Figure 15:
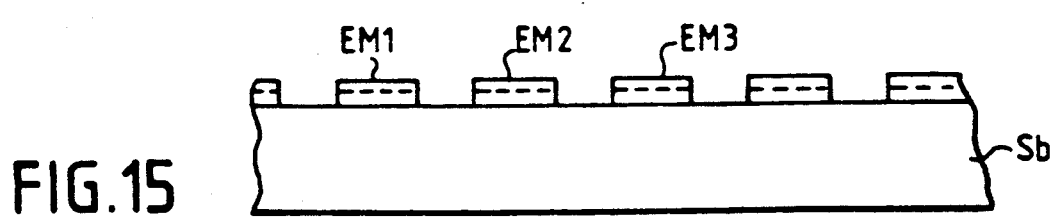
Figure 16:
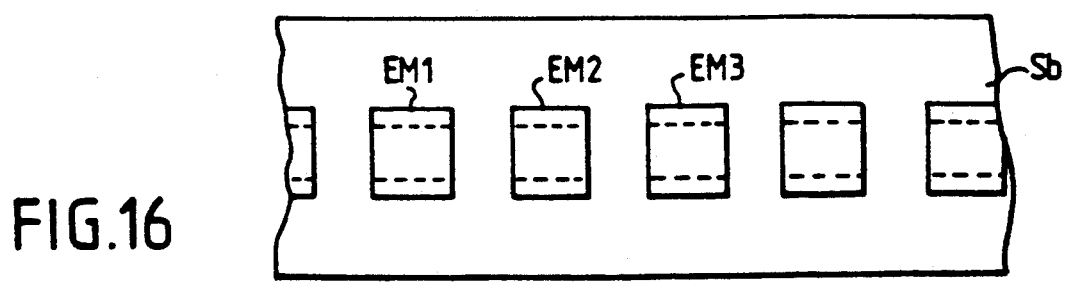

The unit is then heated in such a way that the material of the pads CA1, CA2, CA3 is consumed (or evaporates), the resulting gases escaping by the ends of the pads. There then remains, beneath each element EM1, EM2, EM3 made of devitrifiable enamel, a channel free of material, as is shown in FIGS. 15 and 16.

Figure 17:
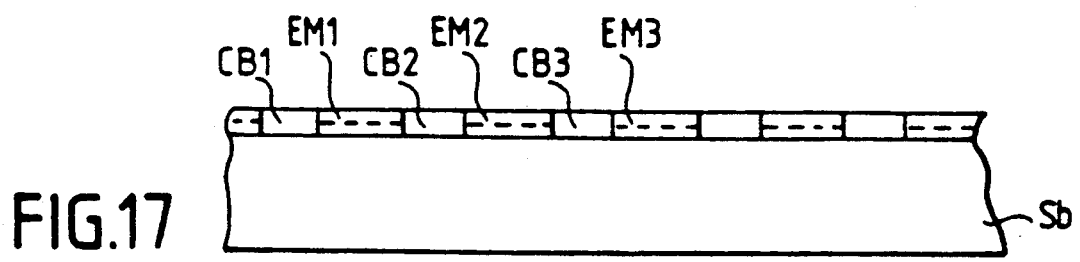
Figure 18:
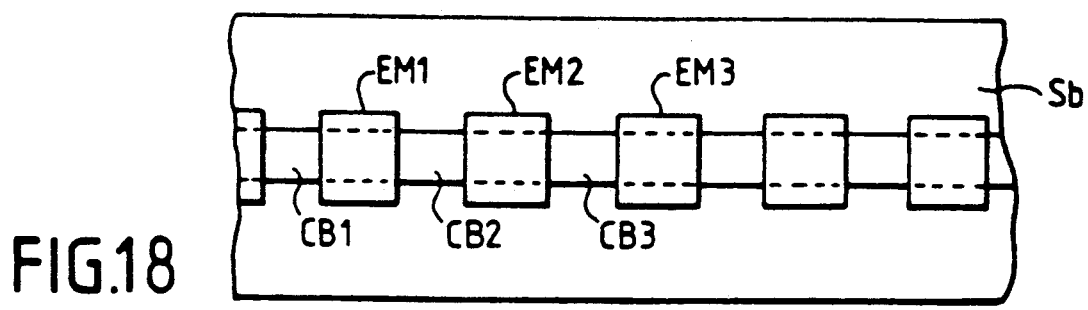
Figure 19:
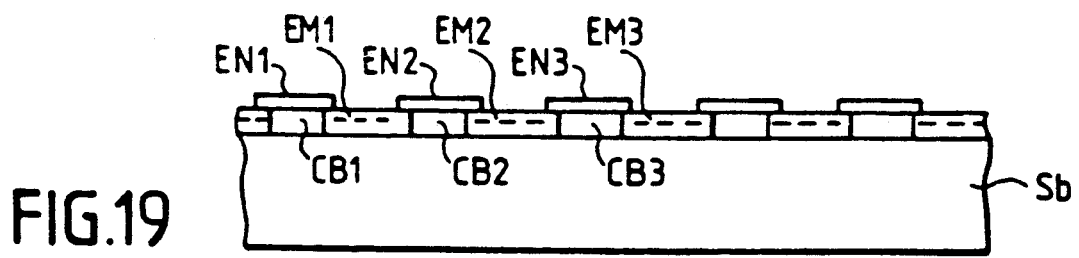

Then, as shown in FIGS. 17 and 18, material of the same type as that of the above pads CA1, CA2, CA3 is deposited between the elements EM1, EM2, EM3 along the layout line of the separating column The elements CB1, CB2, CB3, are obtained. These elements are then coated with a layer of devitrifiable enamel. This can be done either by a uniform layer for the entire device or, as shown in FIG. 19, by elements EN1, EN2, EN3 made of a devitrifiable material, each particular to an element CB1, CB2, CB3.

Figure 20:
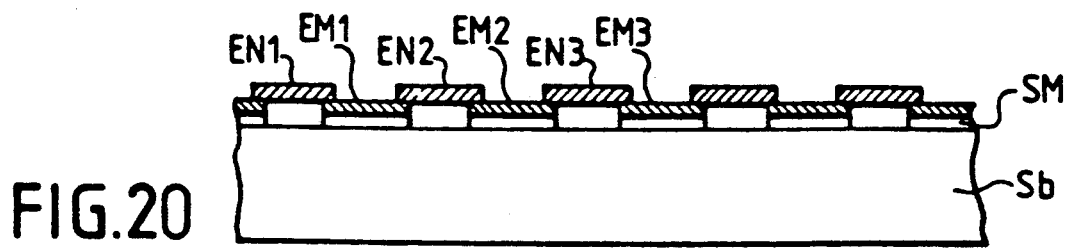

The unit is then re-heated so that the material of the elements CB1, CB2, CB3, is consumed or evaporates. The resulting gases are distributed and then escape through the remaining two free holes of the channel thus formed. The device shown in FIG. 20 is obtained, wherein a channel or a separating column SM is coated with devitrifiable enamel (EM1, EN1 to EM3, EN3).

Figure 21:
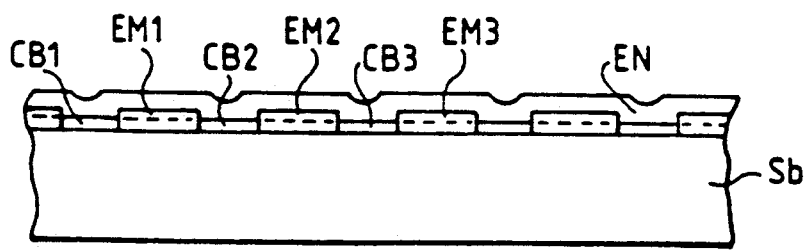
Figure 22:
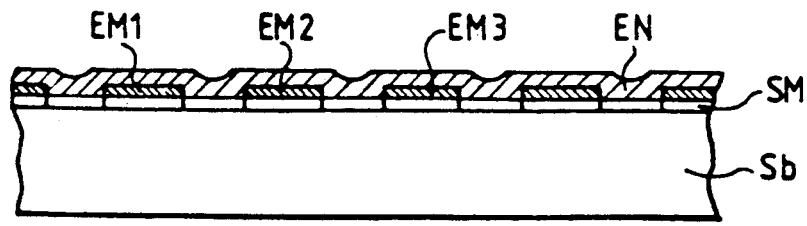

FIGS. 21 and 22 show an alternative manufacturing method according to the invention.

FIG. 21 shows that the elements CB1, CB2, CB3, made between the elements made of devitrifiable material EM1, EM2, EM3, have substantially the same thickness as the elements CA1, CA2, CA3, made previously. The unit is coated with a uniform layer EN of devitrifiable enamel.

After the unit is heated, we thus obtain a separating column or channel SM with substantially even dimensions, covered by the elements EM1, EM2, EM3, and the devitrifiable enamel layer EN.

In general, it is thus seen that the method of the invention can be used to make several different types of devices such as electrochemical sensors, gas-phase chromatographs, etc. requiring a channel or cavity with very small dimensions enabling, for example, a molecular type diffusion of gas.

FIG. 22 shows a sectional view of the channel SM obtained after baking the device of FIG. 21. This channel SM has a substantially constant profile.

The above description has clearly been given purely as a non-restrictive example. Other alternatives can be considered without going beyond the scope of the invention. The numerical examples and choices of materials, in particular, have been given only to illustrate the description.

What is claimed is:

1. An electrochemical sensor for the measurement of relative concentrations of species contained in a fluid mixture, comprising:
   at least one solid electrolyte which is an ion conductor of one of the species of the fluid mixture or of an ion capable of reacting with said species;
   at least one first partial pressure internal reference electrode in contact, by one of its faces, entirely or partly, with the solid electrolyte;
   at least one second measuring electrode in contact, by one of its faces, entirely or partially with the solid electrolyte and receiving the fluid mixture to be analyzed;
   a layer of encapsulating material made of an inert material which is impervious to the species present in the fluid mixture, coating said at least one first electrode, said at least one second measuring electrode, and the solid electrolyte, and having one access hole enabling the fluid mixture to reach the at least one second electrode; and
   at least one microcavity partially covering said at least one second measuring electrode in that zone which covers the electrolyte, said microcavity communicating through the access hole with the fluid mixture to be analyzed and having a thickness enabling a diffusion of a molecular type of fluid.

2. An electrochemical sensor according to claim 1, wherein the thickness of said microcavity is between one and five microns.

* * * * *